(12) United States Patent
Niwa et al.

(10) Patent No.: US 8,724,929 B2
(45) Date of Patent: May 13, 2014

(54) IMAGE ARCHIVE APPARATUS

(75) Inventors: Kenichi Niwa, Otawara (JP); Shini Tanaka, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 978 days.

(21) Appl. No.: 12/196,728

(22) Filed: Aug. 22, 2008

(65) Prior Publication Data

US 2009/0052733 A1 Feb. 26, 2009

(30) Foreign Application Priority Data

Aug. 24, 2007 (JP) ................................ 2007-218793

(51) Int. Cl.
 *G06K 9/54* (2006.01)
 *G06K 9/60* (2006.01)
 *H04N 1/00* (2006.01)

(52) U.S. Cl.
 USPC .......................................... 382/305; 358/403

(58) Field of Classification Search
 CPC ................................................ G06F 17/30265
 USPC .................... 382/100, 305; 358/403; 705/3
 See application file for complete search history.

(56) References Cited

U.S. PATENT DOCUMENTS

| | | | | |
|---|---|---|---|---|
| 6,281,986 B1* | 8/2001 | Form | ............................ | 358/403 |
| 2002/0001468 A1* | 1/2002 | Kaku | ............................ | 396/310 |
| 2003/0068100 A1* | 4/2003 | Covell et al. | .................. | 382/305 |
| 2003/0097070 A1* | 5/2003 | Nakaya et al. | ................. | 600/447 |
| 2005/0108060 A1* | 5/2005 | Sasano | ............................... | 705/3 |
| 2006/0089792 A1* | 4/2006 | Manber et al. | ................ | 701/207 |
| 2007/0232868 A1* | 10/2007 | Reiner | .......................... | 600/300 |
| 2007/0280560 A1* | 12/2007 | Dennison et al. | ............. | 382/305 |
| 2008/0085053 A1* | 4/2008 | Cerosaletti et al. | ........... | 382/190 |
| 2008/0205789 A1* | 8/2008 | Ten Kate et al. | .............. | 382/284 |

FOREIGN PATENT DOCUMENTS

| | | |
|---|---|---|
| JP | 2001-28047 | 1/2001 |
| JP | 2002-345800 | 12/2002 |
| JP | 2003-180636 | 7/2003 |
| JP | 2006-92132 | 4/2006 |
| JP | 2007-21212 | 2/2007 |

OTHER PUBLICATIONS

U.S. Appl. No. 12/039,237, filed Mar. 28, 2008, Kenichi Niwa et al.
Japanese Office Action issued on Jun. 4, 2013, in Japanese Patent Application No. 2012-148768 (in Japanese).

* cited by examiner

*Primary Examiner* — Yubin Hung
(74) *Attorney, Agent, or Firm* — Oblon, Spivak, McClelland, Maier & Neustadt, L.L.P.

(57) ABSTRACT

Conditions regarding attributes of images for generating multi-frame image data including plural frames of images in one file from image data are previously stored. When image data is received, multi-frame image data is generated from the received image data based on incidental information included in the image data and the previously stored conditions. Then, the generated multi-frame image data is archived. When a request for an image is made by a certain terminal, an application functioning on the terminal is identified, and multi-frame image data compliant with the application is transmitted from among the generated multi-frame image data.

5 Claims, 19 Drawing Sheets

FIG. 4

| RECORD NUMBER | STANDARD INFORMATION |
|---|---|
| 01 | • ON SAME AXIS<br>• SAME SLICE THICKNESS<br>• MODALITY (ONLY CT AND MR)<br>• OTHER THAN DIFFUSION IMAGE<br>• OTHER THAN SCOUT IMAGE<br>• SAME SERIES |
| 02 | • ON SAME AXIS<br>• SAME SLICE THICKNESS<br>• SAME SERIES |
| 03 | • ON SAME AXIS<br>• SAME SLICE THICKNESS<br>• SAME IMAGING POSITION GROUP, PER SERIES |
| 04 | • SAME IMAGING POSITION GROUP<br>• CORONAL IMAGE MATRIX<br>• DISPLAY SPECT IMAGE |
| 05 | • ON SAME AXIS<br>• SAME SLICE THICKNESS<br>• SAME IMAGING POSITION GROUP<br>• PLURAL SERIES, PER SERIES |
| 06 | REARRANGE DISPERSED SERIES TO CONTINUOUS SERIES |
| 07 | NORMAL DATA (TO SINGLE DATA) |
|  | . . . |

FIG. 6

INCIDENTAL INFORMATION

| STACID: 1 |
|---|
| TINDEXID: 1 |
| IMAGING AXIS: ○ × |
| SLICE THICKNESS: 1mm |
| MODALITY: CT |
| IMAGE DIAGNOSIS APPARATUS: Modality1 |
| IMAGE TYPE: SCOUT IMAGE |
| IMAGING SITE: HEAD |
| .... |

FIG. 8

| MACHINE TYPE NAME | Stac ID | Tindex ID |
|---|---|---|
| XYZ | SERIES NUMBER | IMAGE NUMBER |
| ABC | IMAGE NUMBER | SERIES NUMBER |
| ... | ... | ... |

FIG. 10

| RECORD NUMBER | DATA TYPE | INCIDENTAL INFORMATION | APPLICATION INFORMATION | ARCHIVE DESTINATION |
|---|---|---|---|---|
| 01 | MULTI-FRAME IMAGE DATA | EXAMINATION ID: 001<br>SERIES ID: 001<br>IMAGE ID: 003<br>IMAGING AXIS: ○×<br>SLICE THICKNESS: 1mm<br>MODALITY: CT<br>IMAGE DIAGNOSIS APPARATUS: Modality1<br>IMAGING SITE: HEAD | XYZ | ABC |
| 02 | SINGLE-FRAME IMAGE DATA | XXX | NONE | YYY |
| 03 | PRE-EDITION INFORMATION | NONE | NONE | DEF |
| ... | ... | ... | ... | ... |

FIG. 16

| RECORD NUMBER | MODALITY INFORMATION | STANDARD INFORMATION |
|---|---|---|
| 01 | X-RAY CT APPARATUS<br><br>MRI APPARATUS | • ON SAME AXIS<br>• SAME SLICE THICKNESS<br>• MODALITY (ONLY CT AND MR)<br>• OTHER THAN DIFFUSION IMAGE<br>• OTHER THAN SCOUT IMAGE<br>• SAME SERIES |
| 02 | · · · | • ON SAME AXIS<br>• SAME SLICE THICKNESS<br>• SAME SERIES |
| 03 | · · · | • ON SAME AXIS<br>• SAME SLICE THICKNESS<br>• SAME IMAGING POSITION GROUP, PER SERIES |
| 04 | · · · | • SAME IMAGING POSITION GROUP<br>• CORONAL IMAGE MATRIX<br>• DISPLAY SPECT IMAGE |
| 05 | · · · | • ON SAME AXIS<br>• SAME SLICE THICKNESS<br>• SAME IMAGING POSITION GROUP<br>• PLURAL SERIES, PER SERIES |
| 06 | · · · | REARRANGE DISPERSED SERIES TO CONTINUOUS SERIES |
| 07 | · · · | NORMAL DATA (TO SINGLE DATA) |
|  |  | · · · |

FIG. 18

| RECORD NUMBER | TERMINAL INFORMATION | STANDARD INFORMATION |
|---|---|---|
| 01 | 15 | • ON SAME AXIS<br>• SAME SLICE THICKNESS<br>• MODALITY (ONLY CT AND MR)<br>• OTHER THAN DIFFUSION IMAGE<br>• OTHER THAN SCOUT IMAGE<br>• SAME SERIES |
| 02 | 10 | • ON SAME AXIS<br>• SAME SLICE THICKNESS<br>• SAME SERIES |
| 03 | 1 | • ON SAME AXIS<br>• SAME SLICE THICKNESS<br>• SAME IMAGING POSITION GROUP, PER SERIES |
| 04 | 1 | • SAME IMAGING POSITION GROUP<br>• CORONAL IMAGE MATRIX<br>• DISPLAY SPECT IMAGE |
| 05 | 1 | • ON SAME AXIS<br>• SAME SLICE THICKNESS<br>• SAME IMAGING POSITION GROUP<br>• PLURAL SERIES, PER SERIES |
| 06 | 1 | REARRANGE DISPERSED SERIES TO CONTINUOUS SERIES |
| 07 | 1 | NORMAL DATA (TO SINGLE DATA) |
|  |  | . . . |

IMAGE ARCHIVE APPARATUS

BACKGROUND OF THE INVENTION

1. Field of the Invention

The present invention relates to an image archive apparatus configured to archive medical images in the format of multi-frame image data.

2. Description of the Related Art

In a hospital, an image diagnosis apparatus configured to image the inside of a subject body and generate medical images, an image archive apparatus configured to archive image data of medical images, and a terminal such as a report creation support apparatus, an image observation apparatus and an image processing apparatus configured to receive archived image data to display images and execute image processing are connected to a network.

The image archive apparatus and the terminal transmit and receive image data by communication via the network. In recent years, the image diagnosis apparatus has become capable of sequentially imaging a subject and generating a large number of medical images because the performance thereof has increased. Therefore, the amount of communication in the transmission and reception of image data between the image archive apparatus and the terminal has become large and has become significant load on the data communication traffic.

Thus, regarding the DICOM standard, a concept of multi-frame image data has been proposed recently in which plural medical image data are recorded in one file, as described in Japanese Unexamined Patent Application Publication JP-A 2007-21212. That is, plural medical image data generated in the image diagnosis apparatus are compiled into one file. The multi-frame image data is also referred to as enhanced data, enhanced DICOM data or enhanced image.

In a case where one image data representing one frame forms one file, communication needs to be established every time one image data is transmitted and received. Therefore, numerous transactions are required between an apparatus for transmitting medical image data and an apparatus for receiving it, and significant load is caused on the data communication traffic. However, in the case of the multi-frame image data, all medical images can be transmitted and received in one communication. Therefore, numerous transactions are not required, whereby the data communication traffic is reduced and increase in communication speed may be expected.

At present, the multi-frame image data is highly flexible in terms of the content of configuration, and it is possible to mix image data of various series of examinations. To be specific, it is possible to mix a scout image used for positioning and an image from main scanning, mix images of different series, mix images with different slice thicknesses or different imaging axes, and mix images with different imaging sites.

On the other hand, in the terminal such as the report creation support apparatus, the image observation apparatus and the image processing apparatus, the types of image data actually used are limited to some extent due to the function thereof. For example, a terminal executing the MPR process does not need a scout image, a diffusion image, images with different slice thicknesses, or images with different imaging axes. That is, because the conventional multi-frame image data includes a large amount of image data unnecessary for a terminal to execute image processing, the terminal needs to divide the image data included in the multi-frame image data into necessary images and unnecessary images in the pre-processing after receiving the multi-frame image data. For a so-called legacy terminal in which a relatively old computer is installed, significant load is required to execute the pre-processing, so that the benefit of the increase in communication of the multi-frame image data is mostly offset. That is, convenience of the multi-frame image data is consequently impaired in the total span from request for transmission of image data to image display or image processing.

SUMMARY OF THE INVENTION

An object of the present invention is to provide an image archive apparatus capable of providing image data requested by a terminal as multi-frame image data to the terminal.

An image archive apparatus according to the present invention comprises: a receiver configured to receive image data including incidental information; a storage configured to store a condition regarding a characteristic of a group of plural frames of images for generating multi-frame image data including plural frames of images in one file from the image data; a generator configured to generate the multi-frame image data, from the image data received by the receiver, based on the incidental information included in the image data and the condition; and an archive configured to archive the multi-frame image data generated by the generator. According to the present invention, it is possible to provide image data required by a terminal to the terminal as multi-frame image data.

BRIEF DESCRIPTION OF THE DRAWINGS

FIG. 4 shows data structure of a standard information table according to the first embodiment.

FIG. 6 shows data structure of a frame information region of multi-frame image data.

FIG. 8 is a table of StacID and TindexID.

FIG. 10 is a data structure view showing part of a database.

FIG. 16 shows data structure of a standard information table according to a third embodiment.

FIG. 18 shows data structure of a standard information table according to a fourth embodiment.

DETAILED DESCRIPTION OF THE EMBODIMENT

Hereinafter, each preferred embodiment of the image archive apparatus according to the present invention will be described in detail with reference to the drawings.

First Embodiment

Figure 1:
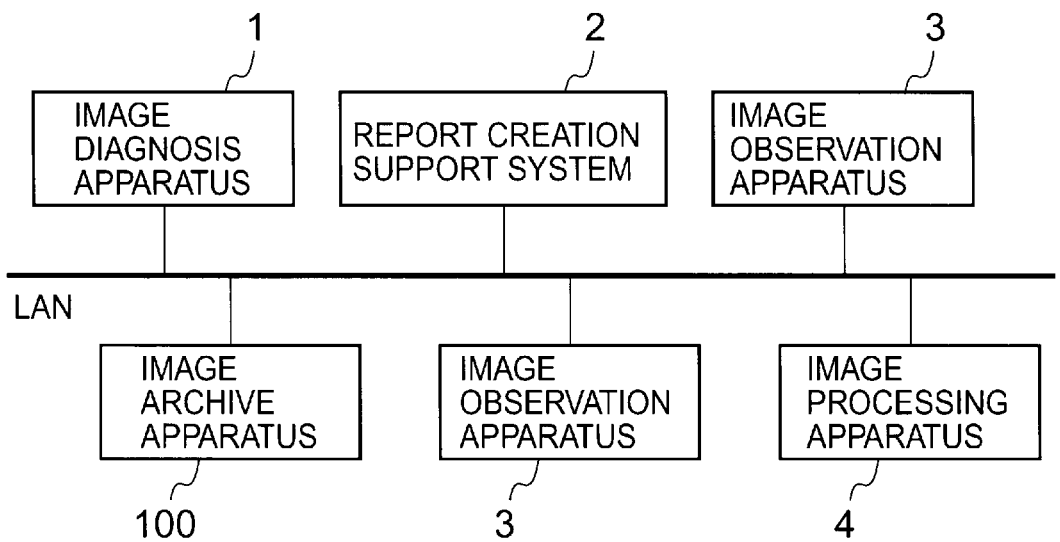
FIG. 1 shows a network to which an image archive apparatus according to a first embodiment is connected.

FIG. 1 is a block diagram showing a network to which an image archive apparatus 100 according to a first embodiment is connected.

The image archive apparatus 100 is connected to a network in a hospital. To this network, an image diagnosis apparatus 1, a report creation support system 2, an image observation apparatus 3, and an image processing apparatus 4 are connected.

The image diagnosis apparatus 1 generates image data of the inside of a subject body. The image diagnosis apparatus 1 sequentially images the inside of the subject body and generates plural medical images. The plural medical images are generated as single-frame image data in which one frame of image data is one file. Moreover, the image diagnosis apparatus 1 may create multi-frame image data in which plural frames of image data having been imaged are compiled into one file. The image diagnosis apparatus 1 transmits the single-frame image data or the multi-frame image data to the image archive apparatus 100.

Upon receiving the single-frame image data or the multi-frame image data, the image archive apparatus 100 archives the data in the form of a database. Then, the image archive apparatus 100 transmits image data corresponding to a request, to a terminal such as the report creation support system 2, the image observation apparatus 3 and the image processing apparatus 4.

The report creation support system 2 receives the image data transmitted from the image archive apparatus 100 and displays the data on a monitor at the time of creation of a report. Otherwise, the report creation system 2 displays a screen for creating a report of the result of observation of the image data displayed on the image observation apparatus 3, on the monitor, to allow creation of the report, and archives the content thereof.

As the image observation apparatus 3, depending on terminals, there is a 3D viewer, a 2D viewer, a fusion viewer, an MR viewer, a viewer for multi-frame image data, or the like. The type of the viewer varies depending on an application software (hereinafter referred to as an application) installed in the image observation apparatus 3. The image observation apparatus 3 receives image data transmitted from the image archive apparatus 100 and displays it on a monitor.

As the image processing apparatus 4, there is a terminal for the MPR process, a terminal for the volume rendering process, a terminal for 4D processing, etc. The type of image processing varies depending on an application installed in the image processing apparatus 4. The image processing apparatus 4 receives image data transmitted from the image archive apparatus 100 and executes the image processing described above.

In the image archive apparatus 100 connected to the network, a group of image data necessary for each of the terminals is prepared on multi-frame image data basis, and is archived in the form of a database.

For example, the characteristic of a group of image data requested by the image processing apparatus 4 varies depending on a function thereof. The characteristic of a group of image data is, for example, the modality type, the position of the imaging axis, the slice thickness, whether it is a functional image or a morphological image, and whether a scout image is included. Depending on the function of the image processing apparatus 4, the characteristic of the group of image data to be requested is different: for example, the modality type is limited, a uniform property of the imaging axis is required, uniformity of the slice thickness is required, and only a functional image or a morphological image is required but a scout image is not required.

For the image processing apparatus 4 in which an application for executing the MPR process is installed, the image archive apparatus 100 archives image data in the form of a database by editing it as multi-frame image data required by the terminal. For example, the content of the configuration of the multi-frame image data is only image data imaged by an X-ray CT apparatus. Furthermore, only image data obtained by imaging a subject with the same slice thickness on the same axis thereof may be the content of the configuration. In addition, image data other than scout images may be the content of the configuration. For the image processing apparatus 4 in which an application for executing the MPR process is installed, multi-frame image data is separately edited and stored in the form of a database.

For example, only image data imaged by an MRI apparatus may be the content of the configuration of the multi-frame image data. In addition, only image data obtained by imaging the subject with the same slice thickness on the same axis thereof may also be the content of the configuration. Furthermore, image data other than diffusion images may also be the content of the configuration. Furthermore, for example, for the image processing apparatus 4 in which an application has been installed for fusion processing via transparent synthesis, multi-frame image data that has been received from the image diagnosis apparatus 1 is archived in the form of a database after separately editing, into multi-frame image data, only image data that has been obtained by imaging a subject with the same slice thickness on the same axis at the same imaging position thereof as the content of the configuration.

Figure 2:
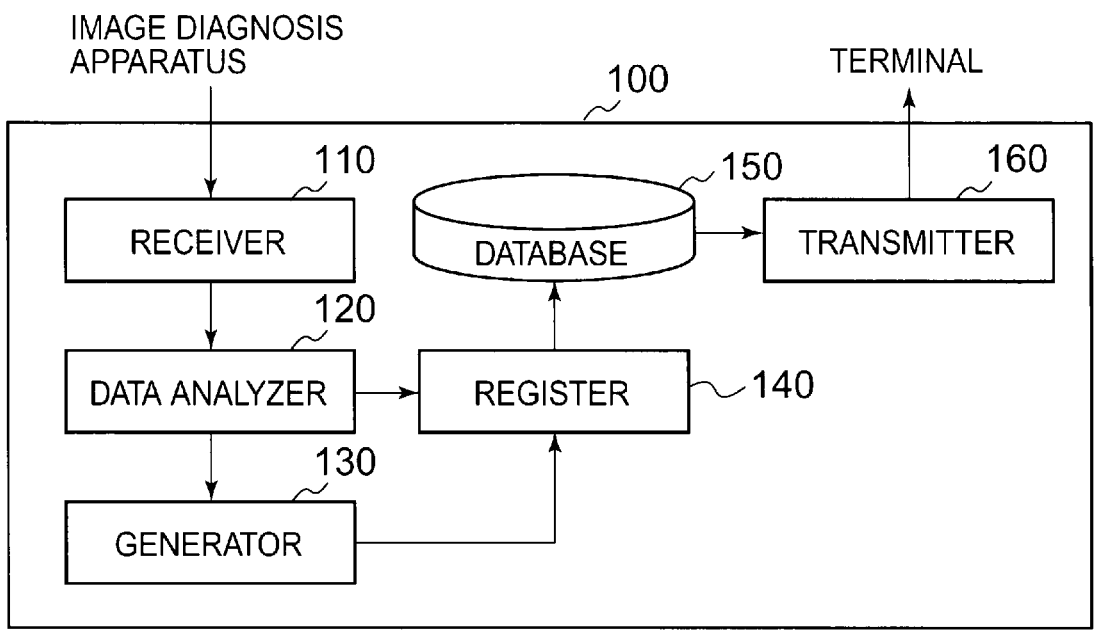
FIG. 2 shows a configuration of the image archive apparatus according to the first embodiment.

FIG. 2 is a block diagram showing the configuration of the image archive apparatus 100 according to the first embodiment. The image archive apparatus 100 comprises a receiver 110, a data analyzer 120, a generator 130, a register 140, a database 150, and a transmitter 160.

The receiver 110 receives image data such as single-frame image data and multi-frame image data from the image diagnosis apparatus 1 via the network. The data analyzer 120 analyzes image data received by the receiver 110 and determines whether the image data is single-frame image data or multi-frame image data. In the case of single-frame image data, the image data is transmitted to the register 140 to be stored in the form of a database. In the case of multi-frame image data, the same is transmitted to the generator 130 for edition.

The generator 130 edits multi-frame image data. The generator 130 has a storage such as a memory, and previously stores standard information indicating the condition regarding the characteristics of a group of image data to be compiled into one file. The standard information indicates the condition of a group of image data to be complied into one file, in accordance with the characteristics of the group of image data. With reference to the standard information, the generator 130 generates multi-frame image data in which image data having the same attributes are compiled, based on the transmitted multi-frame image data. The generator 130 separately compiles, in the form of multi-frame image data, image data that does not belong to any of the multi-frame image data generated based on the respective standard information. Further, the generator 130 generates pre-edition information indicating the configuration content of the multi-frame image data before edition. Here, having the same attribute means being the same within the conditions included in the standard information.

The multi-frame image data generated by the generator 130, the multi-frame image data in which remaining data are compiled, and the pre-edition information are sent to the register 140.

The register 140 archives image data into the database 150. The incidental information of the single-frame image data, the incidental information of the multi-frame image data having been generated by the generator 130, the incidental information of the multi-frame image data in which the remaining image data are compiled, and the pre-edition information are registered into the database 150. The database 150 is composed of a database management system and an image data archive. The database management system, as a server, searches image data requested by a terminal and causes the transmitter 160 to transmit the image data. When a terminal requests transmission of image data with reference to the database 150, the transmitter 160 transmits the requested image data via the network.

Figure 3:
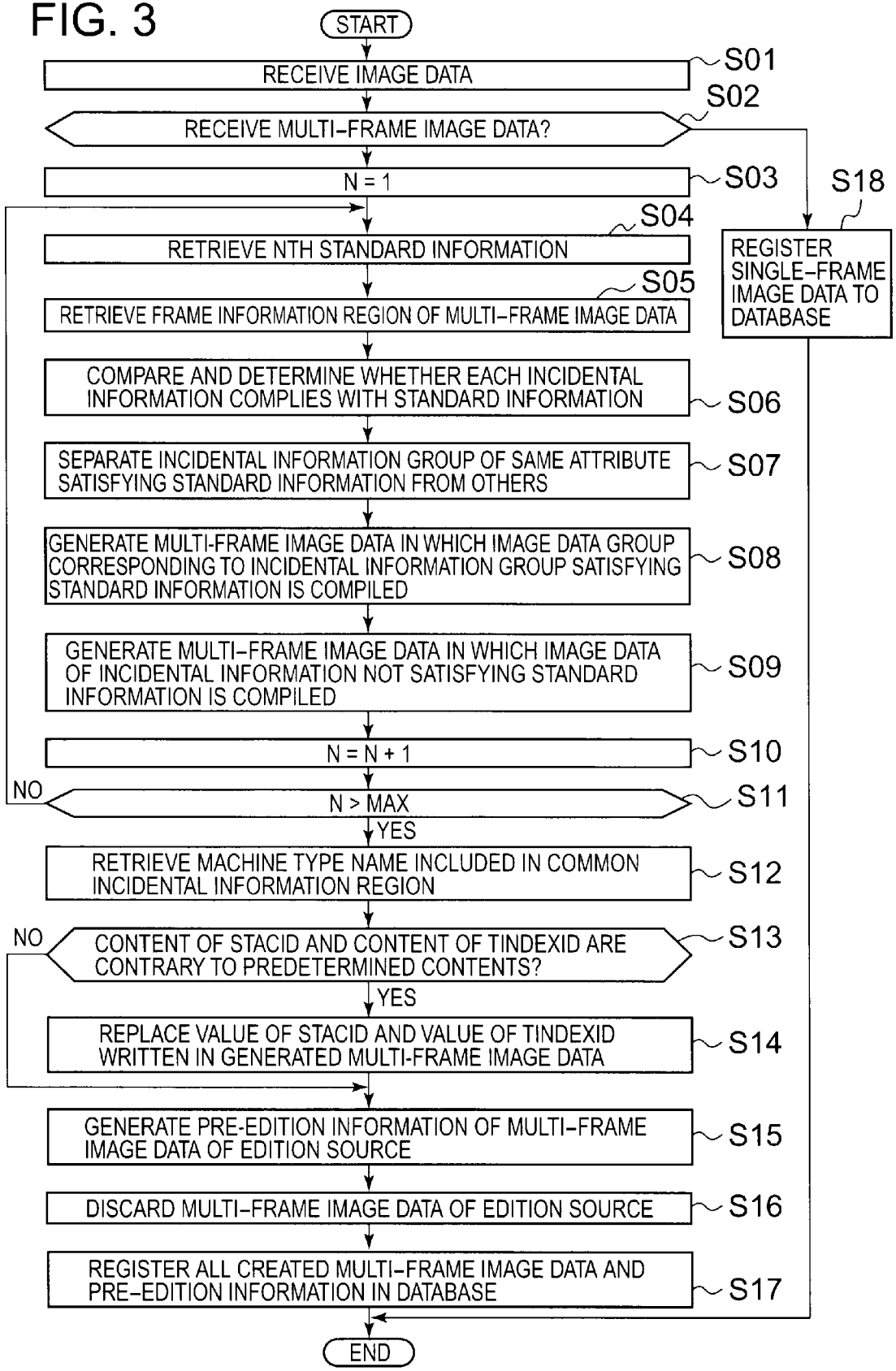
FIG. 3 is a flow chart showing an operation of the image archive apparatus according to the first embodiment.

FIG. 3 is a flow chart showing an operation of the image archive apparatus 100. First, when the image diagnosis apparatus 1 transmits image data to the image archive apparatus 100 via the network, the receiver 110 receives the transmitted image data in step S01. When the receiver 110 receives the image data, the data analyzer 120 determines whether the image data is multi-frame image data or single-frame image data in step S02. In the case of multi-frame image data (S02, Yes), the multi-frame image data is sent to the generator 130. In the case of single-frame image data (S02, No), the register 140 registers the data into the database 150 in step S18, and the edition process at the time of reception ends.

When the multi-frame image data is sent, the generator 130 initializes the record number as N=01 in step S03, and retrieves the standard information of the record number N in step S04. FIG. 4 is a schematic view showing the data structure of a standard information table stored in the generator 130. In the standard information table, standard information indicating the conditions regarding the characteristics of a group of image data to be included in one multi-frame image data are stored. The standard information includes conditions regarding one or more characteristics. In the standard information table, one or more standard information are stored. For example, standard information of record number 01 indicates the condition regarding the characteristics of a group of image data used in the MPR process. Specifically, the standard information includes: a condition of a first characteristic indicating a group of image data having the same imaging axis; a condition of a second characteristic indicating a group of image data having the same slice thickness; a condition of a third characteristic indicating a group of image data having been imaged by an X-ray CT apparatus or an MRI apparatus; a condition of a fourth characteristic indicating a group of image data not including a diffusion image or a scout image; and a condition of a fifth characteristic indicating the same series. Furthermore, for example, standard information of record number 03 indicates a condition regarding the characteristics of a group of image data used in the fusion process. More specifically, the standard information includes: a condition of a first characteristic indicating a group of image data having the same imaging axis; a condition of a second characteristic indicating a group of image data having the same slice thickness; and a condition of a third characteristic indicating a group of image data of the same imaging site. According to the standard information, the type of the image diagnosis apparatus 1 is irrelevant.

Figure 5:
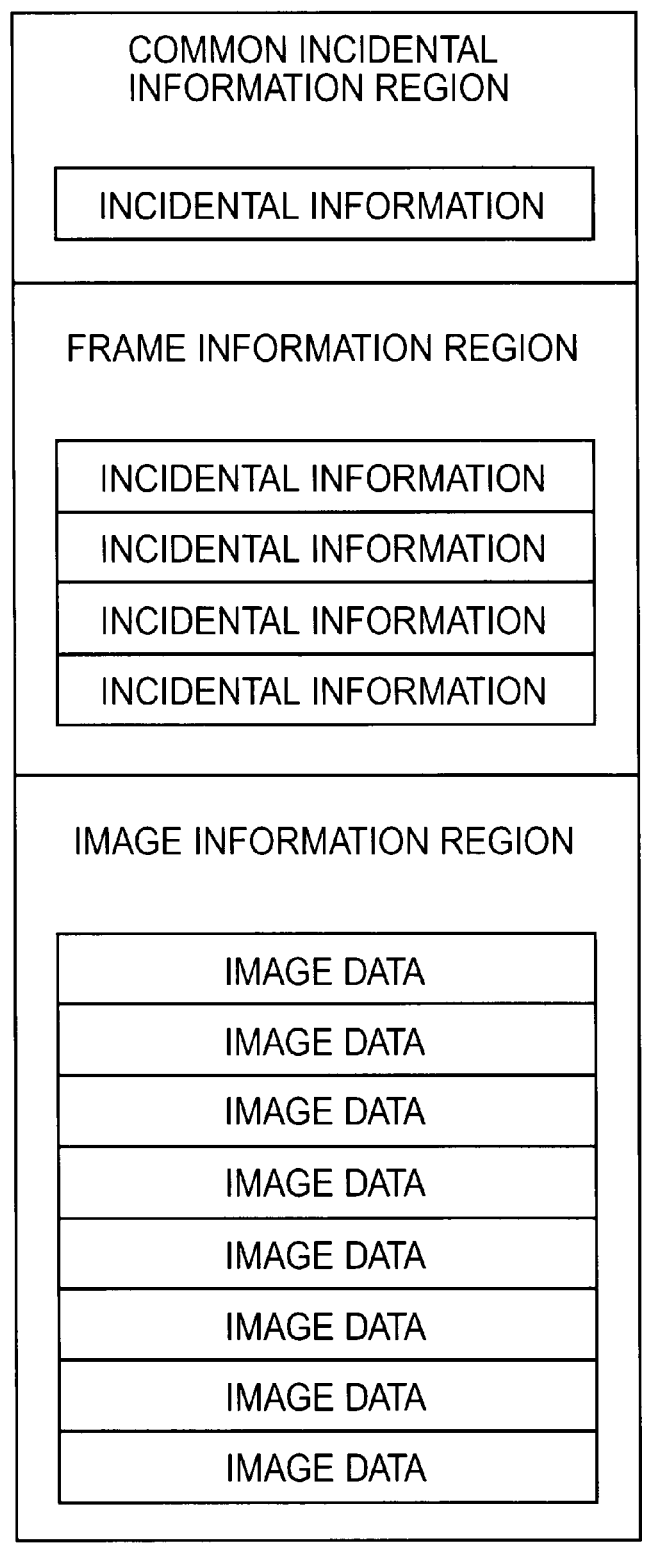
FIG. 5 shows data structure of multi-frame image data.

The generator 130 further retrieves the frame information region of the multi-frame image data in step S05. FIG. 5 is a schematic view showing the data structure of multi-frame image data. The multi-frame image data is composed of three parts: an image information region, a common incidental information region, and a frame information region.

In the image information region, single-frame image data generated by the image diagnosis apparatus 1 are lined up. In the common incidental information region, incidental information that specifies the attribute of the multi-frame image data is written. For example, in the common incidental information region, the patient ID of a subject having been imaged by the image diagnosis apparatus 1, the type, machine name, etc. of the image diagnosis apparatus 1, and the like are written. In the frame information region, individual incidental information of each image data recorded in the multi-frame image data is written. In general, the incidental information listed in the frame information region and the image data listed in the image information region are paired in the listed order. The incidental information in the frame information region are listed in the order according to the order of recording the image data listed in the image information region. Image data listed in the third sheet of the image information region is specified with reference to the third incidental information of the frame information region. Further, instead of correlating incidental information and image data in the listed order, there is a case of attaching common identification information to each of incidental information listed in the frame information region and image data corresponding thereto, thereby linking them. In this case, the image data is specified by referring to the identification information attached to the incidental information.

In step S06, the generator 130 compares the incidental information of the respective image data to determine whether each of the respective incidental information complies with each of the conditions included in the retrieved standard information. In step S07, the respective groups of incidental information having the same attribute satisfying the standard information are separated from the other incidental information. FIG. 6 is a schematic view showing the data structure of incidental information included in the frame information region of the multi-frame image data. In the incidental information included in the frame information region, an identification ID for specifying an image and the attribute of corresponding image data are described. As the identification ID for identifying an image, specifically, a StacID given for each series and a TindexID (Temporary Index ID) for specifying an image within the series are attached. As the attribute of the image data, specifically, information indicating the imaging axis, information indicating the slice thickness, information indicating the attribute of the image diagnosis apparatus 1 having been used in imaging such as "CT," information indicating the machine type name of the image diagnosis apparatus 1 such as "Modality 1," image type information indicating a diffusion image or a scout image, information indicating an imaged site, etc. are written.

The generator 130 compares the respective incidental information of the frame information region in edition with reference to the standard information of record number 01. The image data included in the multi-frame image data are classified so that those having been imaged on the same axis are separated from the rest. Subsequently, the image data are classified so that those with the same slice thickness are separated from the rest. Furthermore, the image data are classified depending on whether the image diagnosis apparatus 1 used for imaging is an X-ray CT apparatus or an MRI apparatus. Moreover, the image data are classified into diffusion images and non-diffusion images. In addition, the image data are classified so that those of the same series are separated from the rest with reference to the StacID. In the classification with regard to the imaging axis, a flag is attached to each of the incidental information in accordance with the value indicated and is in the information included in each incidental information representing the imaging axis. It is also possible to set an ID for identifying each incidental information and to link a flag to the ID.

Moreover, other than this method, any method may be employed as long as distinction is possible. Hereinafter, the method of distinction by attaching a flag will be described. In the classification method related to slice thickness, a flag is attached to each of incidental information in accordance with the value indicated by information representing the imaging axis included in each of incidental information. When separating and classifying whether the image diagnosis apparatus 1 used for imaging is an X-ray CT apparatus or a MRI apparatus, a separate flag is attached respectively to the incidental information that has information representing an X-ray CT apparatus or an MRI apparatus as image diagnosis apparatus 1 and to incidental information other than the former. When separating and classifying images other than diffusion images, a separate flag is attached respectively to the incidental information that has information indicating images other than diffusion images and incidental information that has information indicating diffusion images.

Consequently, from the combination of flags, each of image data within the multi-frame image data may be separated into a group that has incidental information indicating the same attribute by satisfying the standard information of record number 01 and a group that has other incidental information.

Figure 7:
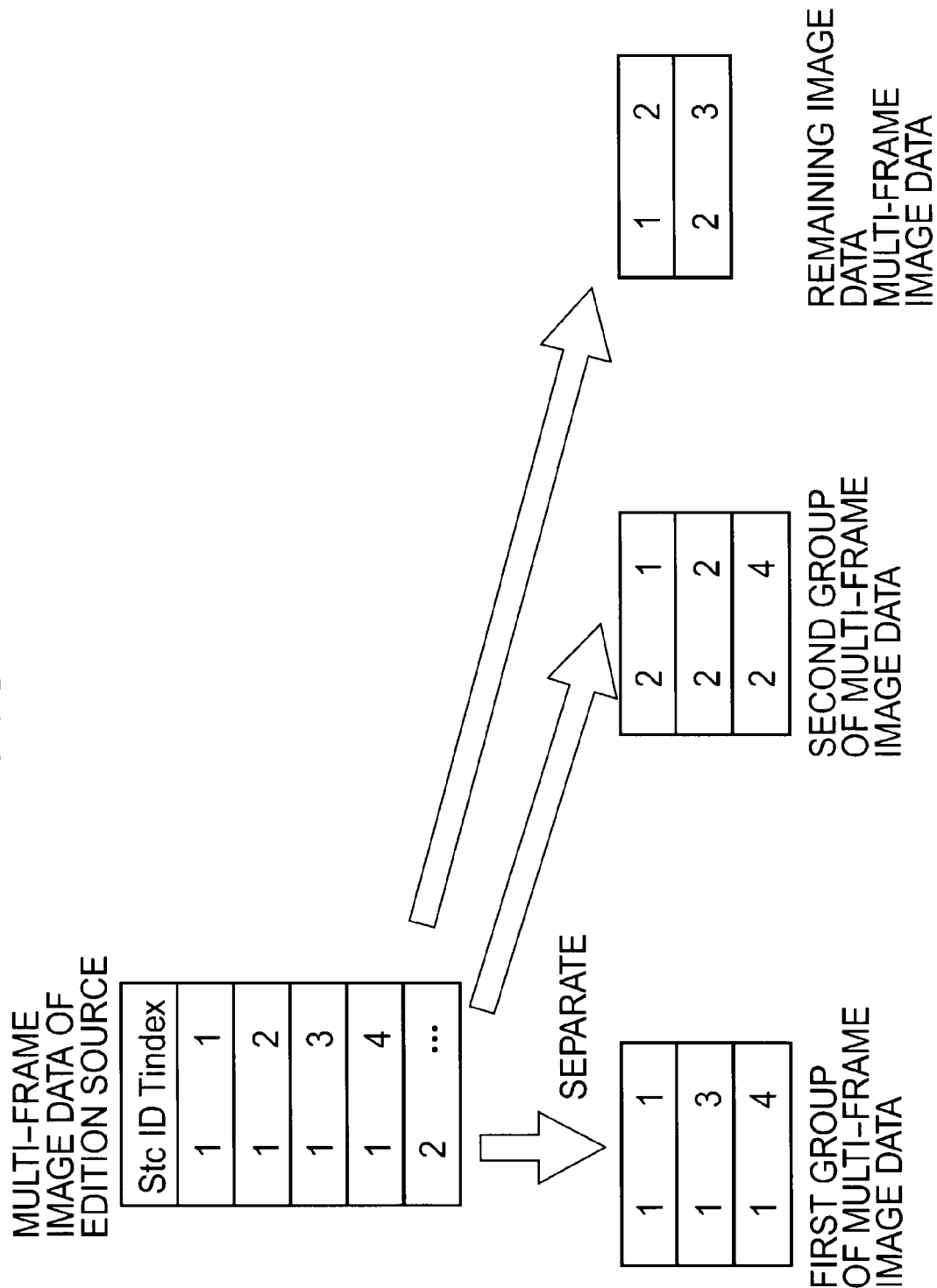
FIG. 7 shows multi-frame image data before and after a generation process according to the first embodiment.

Next, in step S08, as shown in FIG. 7, the generator 130 generates incidental information separated into groups and satisfying the standard information, and multi-frame image data in which image data corresponding to the incidental information are compiled for each group, respectively. Furthermore, in step S09, the generator 130 generates incidental information not satisfying the standard information and multi-frame image data in which image data corresponding to the incidental information are compiled. Consequently, multi-frame image data of a group with the same attribute satisfying one standard information and multi-frame image data of a group of image data not satisfying the standard information are generated.

Then, N=N+1 is set in step S10. In a case where N>Max is not determined in step S11, the generator 130 repeatedly executes the process of steps S04-S09 on the standard information of a new record number N. Max represents the number of stored standard information.

Consequently, multi-frame image data satisfying each of the standard information stored in the standard information table and multi-frame image data not satisfying each of the standard information are generated.

When edition by referring to all of the standard information is finished, the generator 130 redefines the StacID and the TindexID for the incidental information of each of the image data included in the generated multi-frame image data. Some machine types of the image diagnosis apparatus 1 outputting multi-frame image data define that a StacID represents a series number and a TindexID represents an image number. Conversely, some machine types of the image diagnosis apparatus 1 define that a StacID represents an image number and a TindexID represents a series number. So, after receiving the multi-frame image data, the terminal needs to execute pre-processing for interpreting the content of the TindexID and StacID with reference to the information indicating the machine type name. Then, the generator may standardize the content of the StacID and the TindexID within the generated multi-frame image data, to either of them. Specifically, as shown in FIG. 8, a table showing what is indicated by the StacID and the TindexID in correspondence with the name of the machine type of the diagnostic apparatus 1 is stored in the generator 130.

The generator 130, in step S12, retrieves the name of the machine type that is included in the common incidental information region of the multi-frame image data of the edition source and, in step S13, interprets the StacID and the TindexID with reference to the table.

If the content of the StacID and the content of the Tindex ID are contrary to the previously defined content (S13, Yes), in step S14, the value of the StacID and the value of the TindexID in all of the generated multi-frame image data are replaced. For example, it is assumed that a StacID is standardized to a series number and a TindexID is standardized to an image number, and information on the machine type name included in multi-frame image data of an edition source and the table are referred to. If, consequently, the StackID included in the multi-frame image data indicates an image number and the TindexID indicates a series ID, the generator 130 replaces the values of the StackID and the TindexID, which are included in the generated multi-frame image data.

Figure 9:
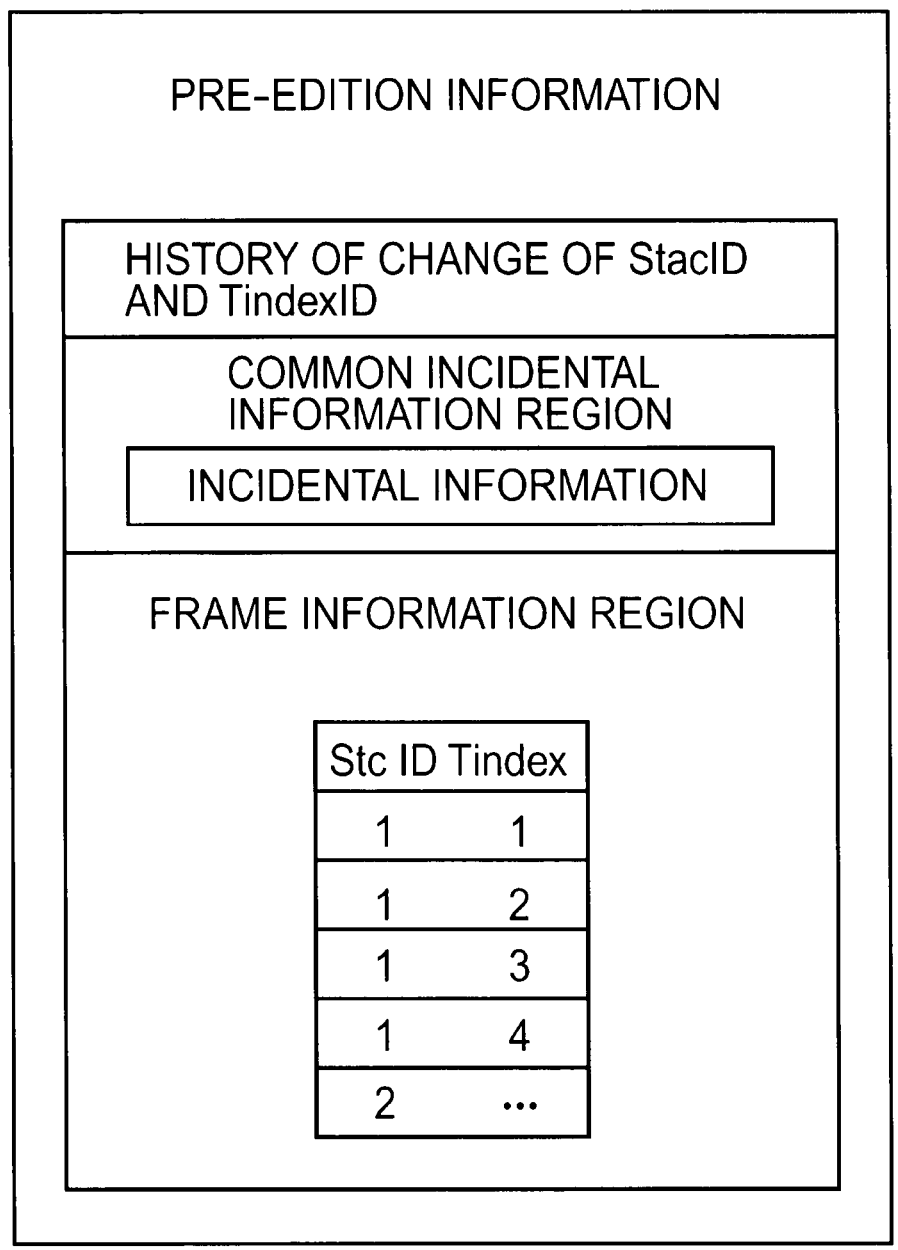
FIG. 9 shows pre-edition information according to the first embodiment.

In step S15, as shown in FIG. 9, the generator 130 generates pre-edition information in which the common incidental information of the multi-frame image data having been the edition source and the frame region information are combined. More specifically, the pre-edition information is information in which the content of the configuration of the multi-frame image data before edition is recorded. It is also possible to include the pre-edition information by extracting only the StacID and the TindexID from the frame region information.

There is a case where the StacID and the TindexID of the generated multi-frame image data are changed because of change of the order, deletion, forwarding of the number, etc. In this case, the history of the change should be included either in the generated multi-frame image data or in the pre-edition information. In step S16, the generator 130 discards the multi-frame image data having been the edition source in order to save capacity. The multi-frame image data having been the edition source may be left if there is no reason for discarding like the capacity saving. In this case, a process of generating the pre-edition information may be omitted.

When the processing by the generator 130 is finished, the register 140 registers and archives, into the database 150, multi-frame image data having been compiled to satisfy the standard information, multi-frame image data having been generated by compiling the remaining image data in one file, and the pre-edition information in step S17. Furthermore, the register 140 links application identification information corresponding to the standard information having been used for generation of the multi-frame image data, to the multi-frame image data, and records into the database 150. The application identification information is information identifying an application.

The register 140 previously stores a table of the application identification information and information identifying the standard information. The register 140 records by linking the application identification information corresponding to the standard information having been used for generation of the multi-frame image data, to the multi-frame image data.

As described above, in the image archive apparatus 100 of the present embodiment, image data is divided according to the standard information indicating the condition regarding the characteristics of a group of image data, and multi-frame image data is recompiled and stored. In a case where image data satisfying plural standard information distinguished by record numbers exists, the recompiled multi-frame image data may redundantly include the same frame. By storing, as standard information, each condition regarding the attribute of image data required by each terminal such as the report creation support system 2, the image observation apparatus 3, and the image processing apparatus 4, at the time of transmission of image data to each terminal, only required image data may be transmitted in the format of multi-frame image data that is composed of necessary data having the StacID and the TindexID with the standardized content.

Therefore, in addition to the enhancement of the communication speed owing to the multi-frame image data, a process of extracting only the image data that is required for processing by analyzing the multi-frame image data in each terminal may be omitted, thus making it possible to reduce the time from the request for image data to the main processing of the image data by each terminal. Moreover, because the analysis of the StacID and the TindexID may be omitted, the time up to the main processing may be shortened accordingly. For example, by compiling only image data required for the MPR processed and stored after compiling the same into multi-frame image data in which a scout image, etc., has previously been left out, the terminal does not need to leave out unnecessary image data in the MPR processing from the multi-frame image data that has been received for the MPR processing.

Standard information stored in a standard information table may be only one, but even if plural standard information are stored, the standard information to be used may be singular. In the case of selecting one standard information from among a plurality of sets of standard information, only a response to input from an operator using a mouse or a keyboard is required. If selection has been entered in advance, identification information indicating being information to be used should be attached to the standard information to be used.

Next, a mode of transmission of the multi-frame image data will be described. The database management system searches image data with reference to incidental information and application identification information recorded in the database 150.

FIG. 10 is a schematic view showing part of the database 150 of stored images. In the database 150, the incidental information and archive destination of single-frame image data, the incidental information and application identification information of multi-frame image data, the archive destination of this image data, and the pre-edition information are stored. In the incidental information, information indicating an imaging shaft, information indicating a slice thickness, information indicating the type of image diagnosis apparatus 1 such as "CT" used in imaging, information indicating the name of the machine type of the image diagnosis apparatus 1 such as "Modality 1", information indicating a diffusion image or a scout image, information indicating an imaging area, etc., are described.

Figure 11:
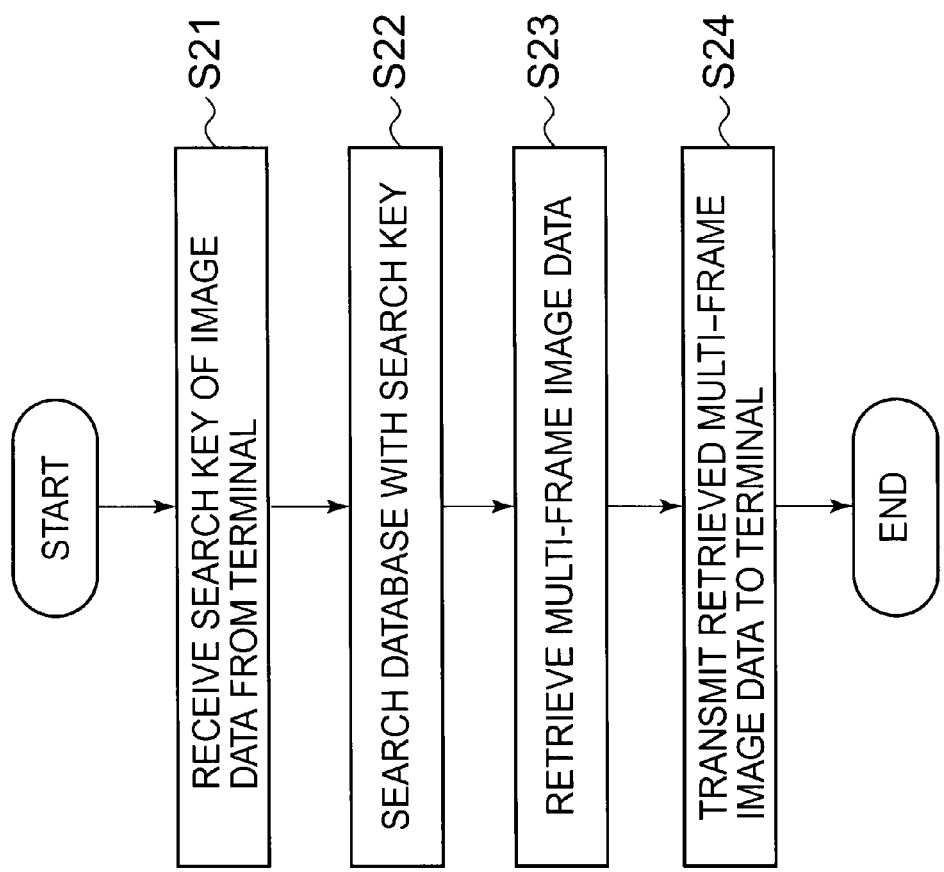
FIG. 11 is a flow chart showing an operation of transmitting image data.

FIG. 11 is a flow chart showing an operation of transmitting image data. In step S21, the transmitter 160 receives a key for searching image data, from a terminal. The search key includes incidental information of requested image data and application identification information for identifying the application having requested the image data. The database management system searches the database 150 by using the search key in step S22, and retrieves corresponding multi-frame image data in S23. The transmitter 160 transmits the retrieved multi-frame image data to the terminal in S24.

Here, instead of linking multi-frame image data and application identification information on the database 150, it is possible to write application identification information in multi-frame image data. When multi-frame image data is generated, the register 140 writes information for identifying an application corresponding to standard information having been used for the generation, into the multi-frame image data. The database management system searches the application identification information having been written in the multi-frame image data, and retrieves the requested multi-frame image data. In this case, the extension of the data is also included in the application identification information.

It is also possible to configure to show the terminal a list of image data compliant with the incidental information and cause the terminal to select from the list.

Second Embodiment

The first embodiment describes an example in which a process of editing multi-frame image data is executed at the time of reception of the multi-frame image data. Additionally, it is also possible to configure to generate multi-frame image data from a plurality of single-frame image data. The image archive apparatus 100 according to a second embodiment generates multi-frame image data from a plurality of single-frame image data.

Figure 12:
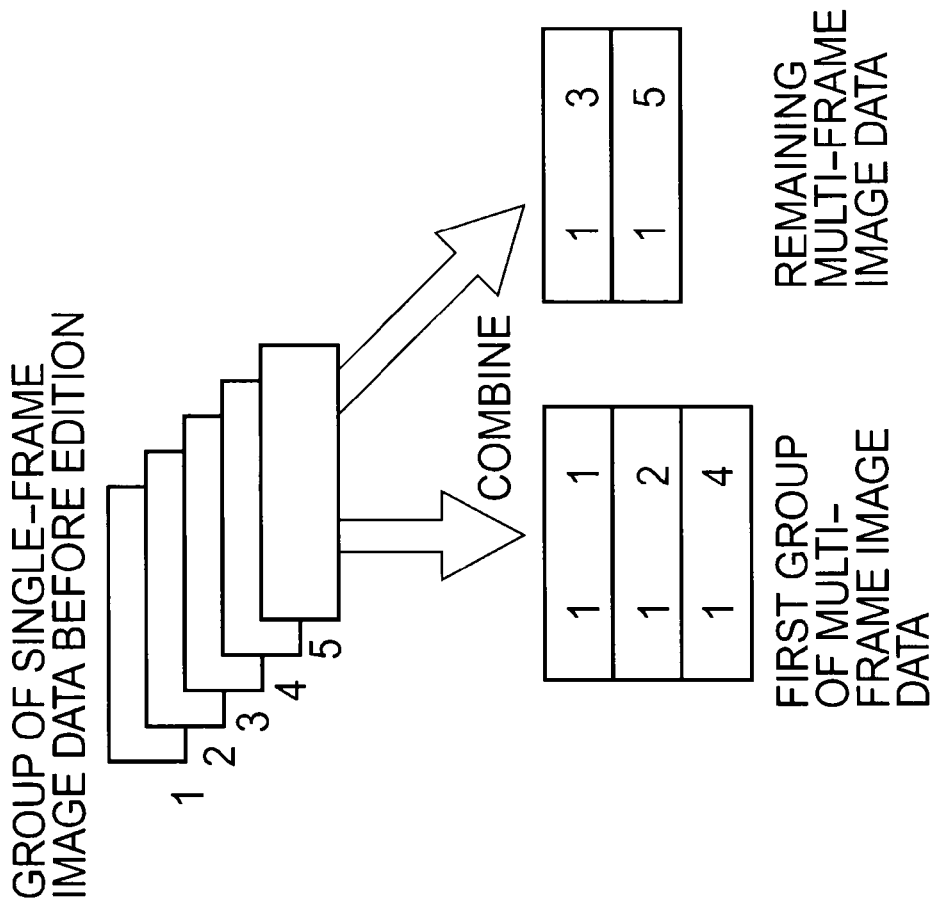
FIG. 12 shows an example of conversion of a plurality of single-frame image data into multi-frame image data.

When a plurality of single-frame image data are transmitted from the image diagnosis apparatus 1, the generator 130 executes the edition process on the single image data. FIG. 12 is a schematic view showing an example of converting a plurality of single-frame image data to multi-frame image data. As shown in FIG. 12, the generator 130 specifies a single-frame image data group satisfying the condition included in the standard information, from among the plurality of single frame image data. Then, the generator compiles the single-frame image data group into one file to generate multi-frame image data.

Further, the generator compiles single-frame image data not satisfying the condition included in the standard information into one to generate multi-frame image data.

Figure 13:
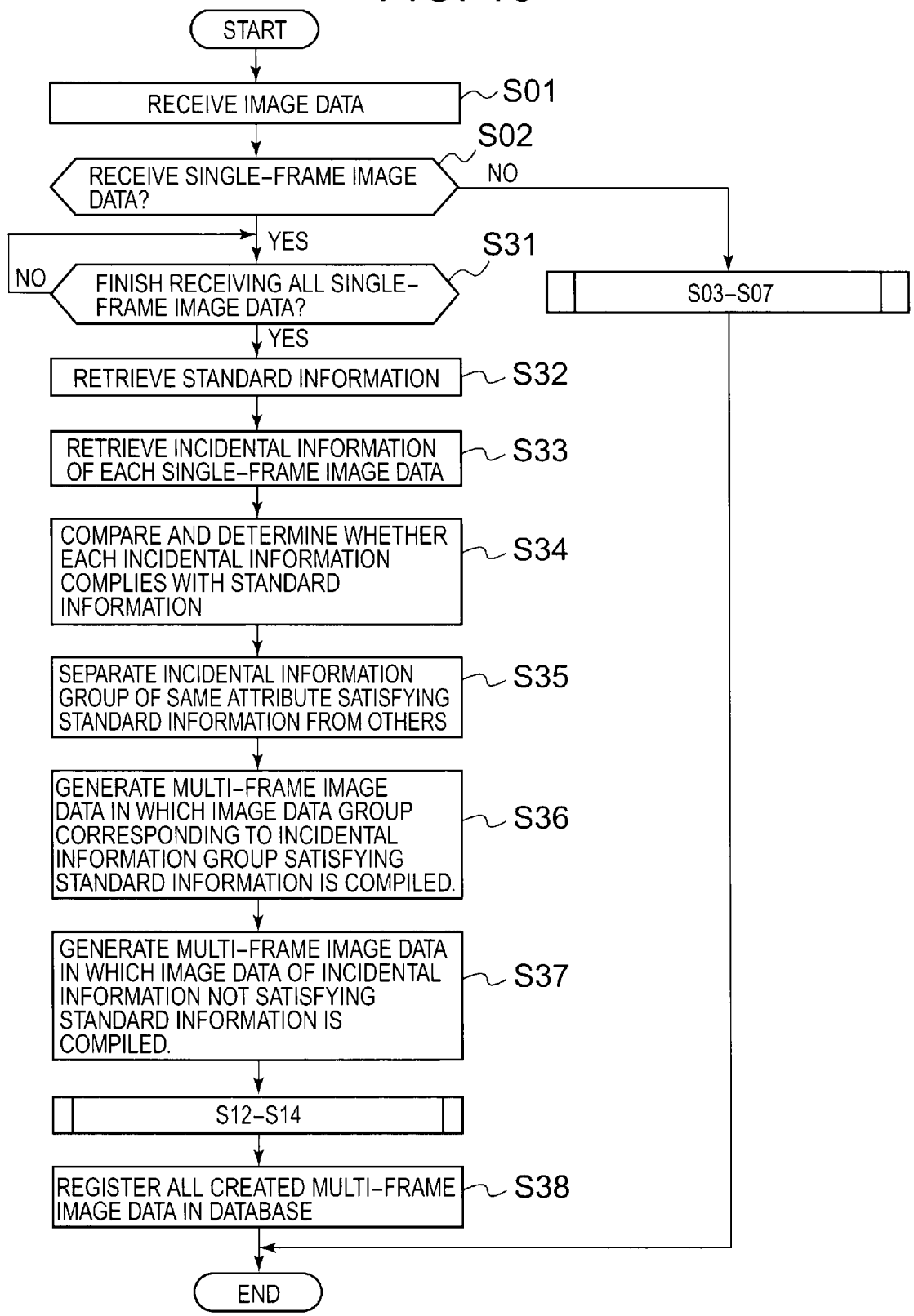
FIG. 13 is a flow chart showing an operation of conversion of a plurality of single-frame image data into multi-frame image data.

FIG. 13 is a flow chart showing an operation of converting a plurality of single-frame image data to multi-frame image data. To simplify the explanation, it is assumed that standard information stored in the standard information table is only one, but a plurality of standard information may be stored. First, when the image diagnosis apparatus 1 transmits image data to the image archive apparatus 100 via the network, the receiver 110 receives the transmitted image data in step S01. When the receiver 110 receives the image data, the data analyzer 120 determines whether the image data is multi-frame image data or single-frame image data in step S02. In the case of multi-frame image data (S02, No), the process from step S03 to step S17 according to the first embodiment is executed. In the case of single-frame image data (S02, Yes), when reception of all of a plurality of transmitted single-image data is completed in step S31 (S31, Yes), the multi-frame image data is sent to the generator 130. The generator 130 retrieves the standard information in step S32, and retrieves the incidental information of each of the single-frame image data in S33.

In step S34, the generator 130 compares to determine whether each of the incidental information complies with the condition included in the retrieved standard information, and separates each group of incidental information satisfying the standard information in step S35 and representing the same attribute, from the rest of the incidental information. Next, in step S36, the generator 130 generates multi-frame image data in which the single-frame image data separated into each group are compiled for each group. Furthermore, in step S37, the generator 130 generates multi-frame image data in which the single-frame image data not satisfying the standard information are compiled.

Consequently, each multi-frame image data of the same attribute group satisfying the condition included in one standard information and multi-frame image data of a group of image data not satisfying the standard information are generated.

Then, the generator 130 executes the process from step S12 to step S14 to redefine the StacID and the TindexID, and thereafter, registers the generated multi-frame image data into the database 150 in step S38.

Figure 14:
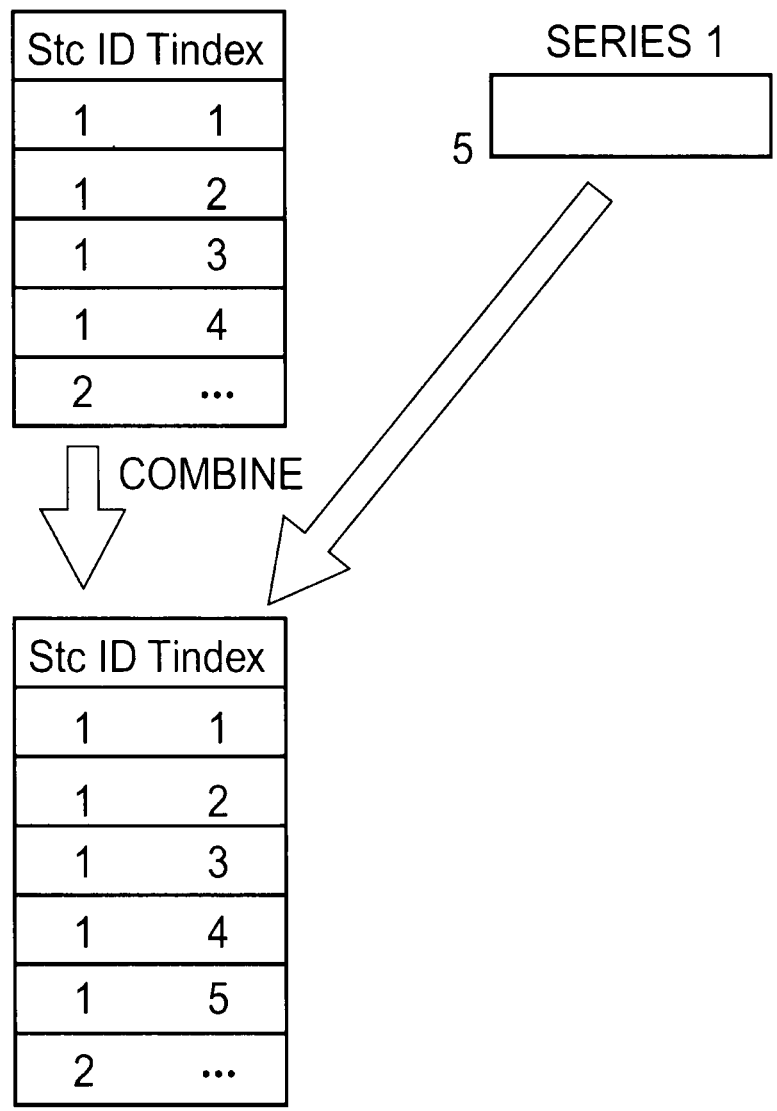
FIG. 14 shows a process of inserting single-frame image data into multi-frame image data.

Further, the generator 130 may regularly execute the process of converting into multi-frame image data to convert the single-frame image data having already been stored in the database 150 into multi-frame image data. At this moment, as shown in FIG. 14, in a case where there is single-frame image data that can be compiled into multi-frame image data having been generated already, the single-frame image data may be added to the multi-frame image data.

Figure 15:
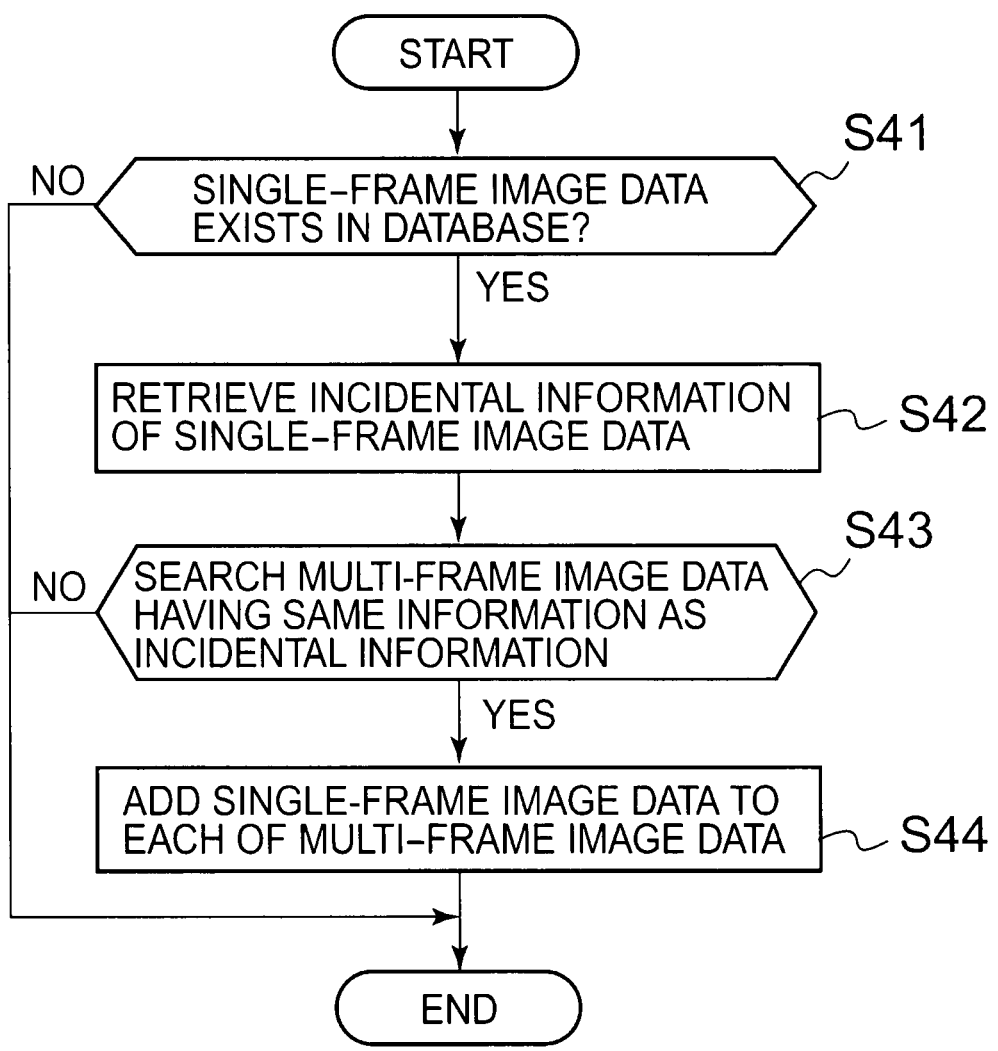
FIG. 15 is a flow chart showing an operation of adding single-frame image data to multi-frame image data.

FIG. 15 is a flow chart showing an operation of adding single-frame image data to multi-frame image data. First, when single-frame image data exists in the database 150 in step S41 (S41, Yes), the generator 130 retrieves the incidental information of the single-frame image data in step S42.

Furthermore, in step S43, with reference to the database 150, the generator 130 searches multi-frame image data having the same information as the retrieved incidental information in the common incidental information and in the incidental information of the frame information region. In a case where one or two or more corresponding multi-frame image data are found (S43, Yes), the single-frame image data is added to each of the found multi-frame image data in S44. To be specific, the incidental information of the single-frame image data is recorded in the frame information region, and the image data portion of the single-frame image data is recorded in the image information region.

Third Embodiment

In the first embodiment, multi-frame image data is generated for each of the stored standard information. In the image archive apparatus 100 according to a third embodiment, priority conditions are prepared, and multi-frame image data corresponding to standard information satisfying the priority conditions is generated and archived. This is because, depending on the performance of the image archive apparatus 100 (such as the arithmetic processing ability and the storage capacity), creating and archiving multi-frame image data corresponding to each of the standard information stored in the standard information table may be a significant load on the image archive apparatus 100.

FIG. 16 is a schematic vie showing the standard information table according to the third embodiment. As shown in FIG. 16, modality information is linked to the standard information. The modality information is information indicating the type of the image diagnosis apparatus 1. How multi-frame image data will be processed afterward can be predicted to some extent based on the type of the image diagnosis apparatus 1. For example, image data derived from an X-ray CT apparatus is highly likely to be subjected to 3D volume rendering, and is also highly likely to be subjected to the MPR process. The generator 130 generates multi-frame image data by using the standard information linked to the modality information compliant with information indicating the type of the image diagnosis apparatus 1 included in the received multi-frame image data.

Figure 17:
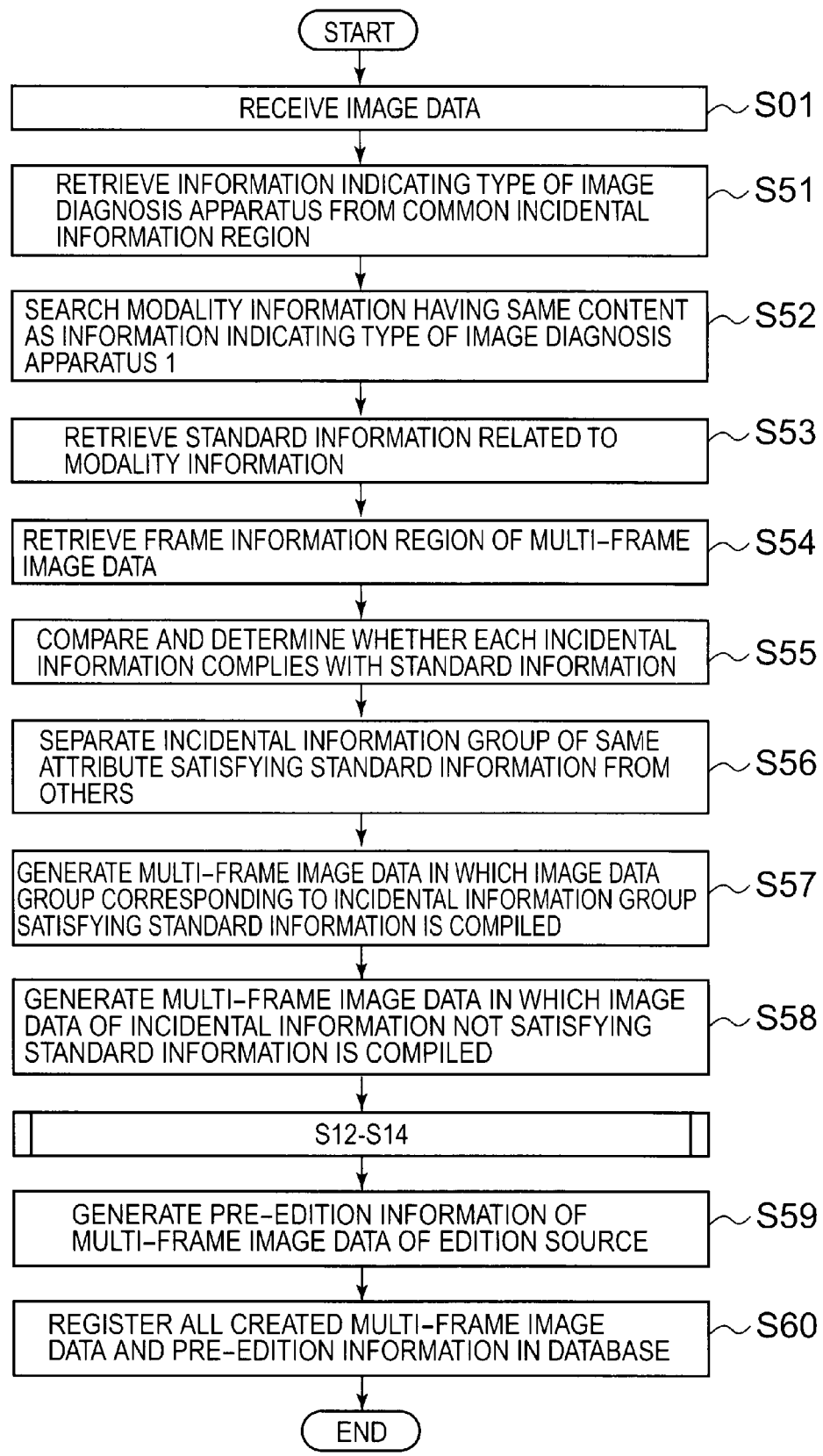
FIG. 17 is a flow chart showing an operation of generating multi-frame image data according to the third embodiment.

FIG. 17 is a flow chart showing an operation of generating multi-frame image data according to the third embodiment. In the following explanation, on the premise that multi-frame image data is received, the explanation of the process of determining whether to be multi-frame image data or single-frame image data will be omitted. As described in the second embodiment, multi-frame image data may be generated from single-frame image data in the event of receiving single-frame image data. Also in this case, it is possible to apply the standard information to which the modality information is linked shown in FIG. 16.

First, when the image diagnosis apparatus 1 transmits image data to the image archive apparatus 100 via the network, the receiver 110 receives the transmitted image data in S01.

When multi-frame image data is sent, the generator 130 retrieves information indicating the type of the image diagnosis apparatus 1 from the common incidental information region of the multi-frame image data in step S51. In step S52, the generator 130 searches, with reference to the standard information table, modality information having the same content as the information indicating the type of the image diagnosis apparatus 1. When the modality information is found, the generator retrieves standard information linked to the modality information in step S53. Furthermore, in step S54, the generator 130 retrieves the frame information region of the multi-frame image data.

The generator 130 compares to determine whether incidental information of each incidental information complies with the condition included in the retrieved standard information in step S55, and separates each group of the incidental information indicating the same attribute by satisfying the standard information, from the rest of the incidental information in step S56. Next, in step S57, the generator 130 generates multi-frame image data in which the incidental information separated into each group and the corresponding image data are compiled for each group. Furthermore, in step S58, the generator 130 generates multi-frame image data in which incidental information not satisfying the standard information and the corresponding image data are compiled.

Then, the generator 130 executes the process from step S12 to step S14 to redefine the StacID and the TindexID, and thereafter, the generator 130 generates pre-edition information in step S59. Finally, in step S60, the register 140 registers and archives, in the database 150, each of the multi-frame image data compiled so as to satisfy the conditions included in the standard information, the multi-frame image data generated by compiling the remaining image data into one file, and the pre-edition information. In a case where there are a plurality of modality information compliant with the information indicating the type of the image diagnostic apparatus 1 having been retrieved from the common incidental information region, the process of generating multi-frame image data is repeatedly executed on standard information linked to each.

In the image archive apparatus 100 according to the third embodiment, multi-frame image data with frequently used configuration content is generated and edited, whereby load on the image archive apparatus 100 is reduced, and a function as an image server, which is a process that the image archive apparatus 100 executes originally, is not impaired.

Fourth Embodiment

Figure 19:
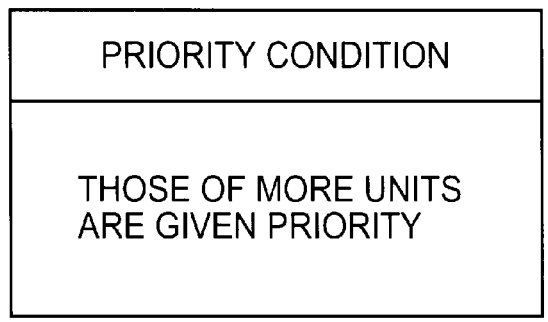
FIG. 19 shows a priority condition table.

A fourth embodiment is a modification of the image archive apparatus 100 in the case of generating multi-frame image data by using part of a plurality of standard information. FIG. 18 is a schematic view showing the data structure of a standard information table according to the fourth embodiment. In the standard information table, terminal information is linked to standard information and stored. The terminal information is information on a terminal that requires multi-frame image data satisfying the linked standard information. For example, the terminal information is information indicating the number of terminals requiring multi-frame image data satisfying the linked standard information. FIG. 19 is a schematic view showing a priority condition table. The generator 130 previously stores the priority condition table. In the priority condition table, a priority condition is previously stored. The priority condition is selected by entry with a mouse, keyboard, etc., and stored into the priority condition table. The priority condition corresponds to the content of the terminal information. For example, the priority information is information indicating that a larger number of terminals are given priority, or information indicating that ten or more terminals are given priority.

With reference to the priority condition table and the terminal information, the generator 130 retrieves the standard information linked to the terminal information satisfying the priority condition, and edits multi-frame image data satisfying the retrieved standard information. In a case where there are a plurality of priority conditions, standard information linked to terminal information satisfying all of the priority conditions is retrieved. Moreover, standard information linked to terminal information not satisfying the priority condition is not used, or is used in a case where load on the image archive apparatus 100 is a specified value or less.

Figure 20:
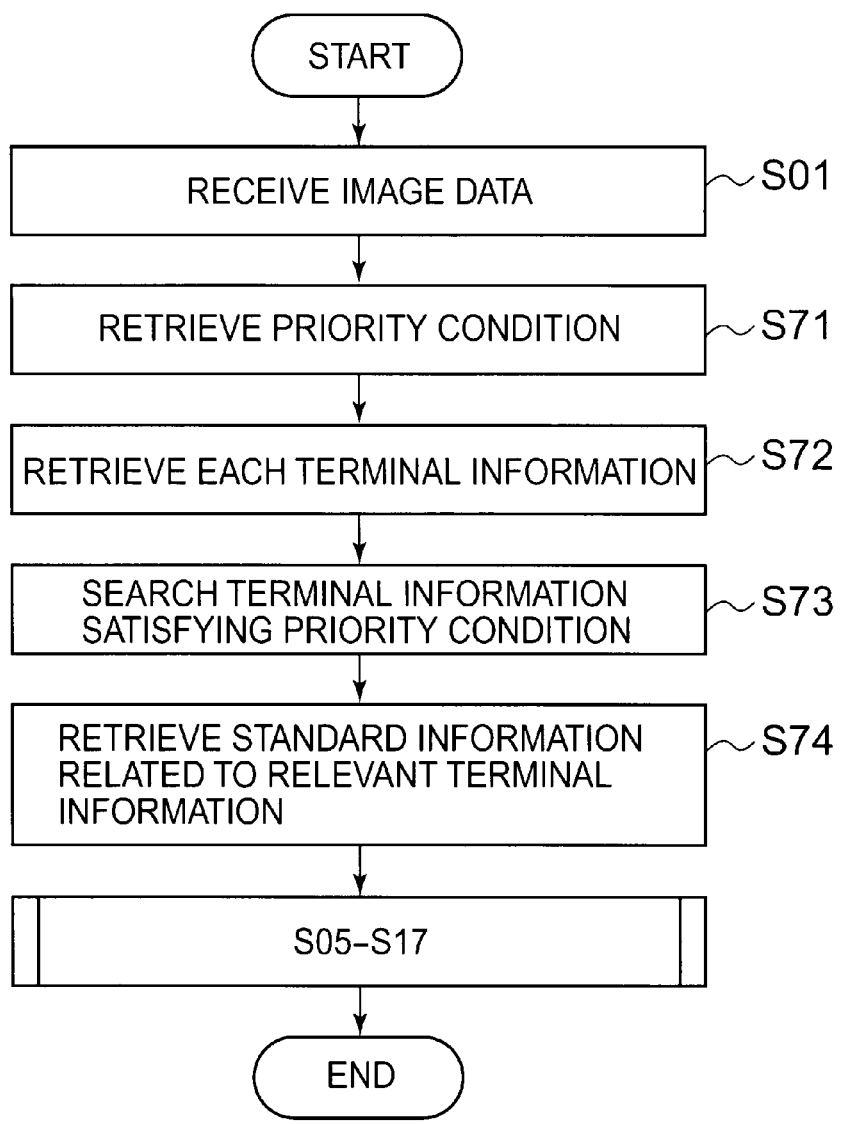
FIG. 20 is a flow chart showing an operation of the image archive apparatus according to the fourth embodiment.

FIG. 20 is a flow chart showing the operation of the image archive apparatus 100 according to the fourth embodiment. Because the operation after retrieving the standard information is the same as in the first embodiment, the detailed explanation thereof will be omitted.

First, when the image diagnosis apparatus 1 transmits image data to the image archive apparatus 100 via the network. In step S01, the receiver 110 receives the transmitted image data. When the multi-frame image data is sent, the generator 130 retrieves the priority condition from the priority condition table in step S71, and retrieves each of the terminal information of the standard information table in step S72.

Here, it is assumed that it is written as the priority information that a larger number of terminals are given priority.

After retrieving the priority condition and the terminal information, the generator 130 searches terminal information satisfying the priority condition in step S23. When the terminal information satisfying the priority condition is found, the generator 130, in step S24, retrieves standard information linked to the terminal information, and executes edition of the multi-frame image data and registration thereof into the database 150 from step S04 to step S11, thereby ending the process. In a case where the priority condition is that a larger number of terminals are given priority, the generator 130 searches a largest number of terminals indicated by the terminal information, and uses standard information linked to the terminal information.

Instead of the terminal information, frequency information may be set as the priority condition. To the pair of standard information and frequency information, information identifying a terminal is linked. To standard information indicating the condition of image data required by the terminal, information identifying the terminal is linked. The frequency information is linked to each of standard information. The frequency information is the number of times that image data has been requested.

Every time a request for image data is made, the transmitter 160 adds a count of 1 to the frequency information linked to information identifying the terminal having requested the image data. The generator 130 retrieves the standard information having been paired with the frequency information having the maximum value or a value within a certain rank from the top, and generates multi-frame image data.

Fifth Embodiment

In the case of generating multi-frame image data by using part of the standard information based on the priority condition or the modality information, there is a case where multi-frame image data composed of a group of image data required by an application functioning on another terminal does not exist. In this case, multi-frame image data of an edition source is restored by referring to the pre-edition information, and the multi-frame image data is transmitted after being edited so as to satisfy standard information according to a function required by the terminal having requested an image.

Figure 21:
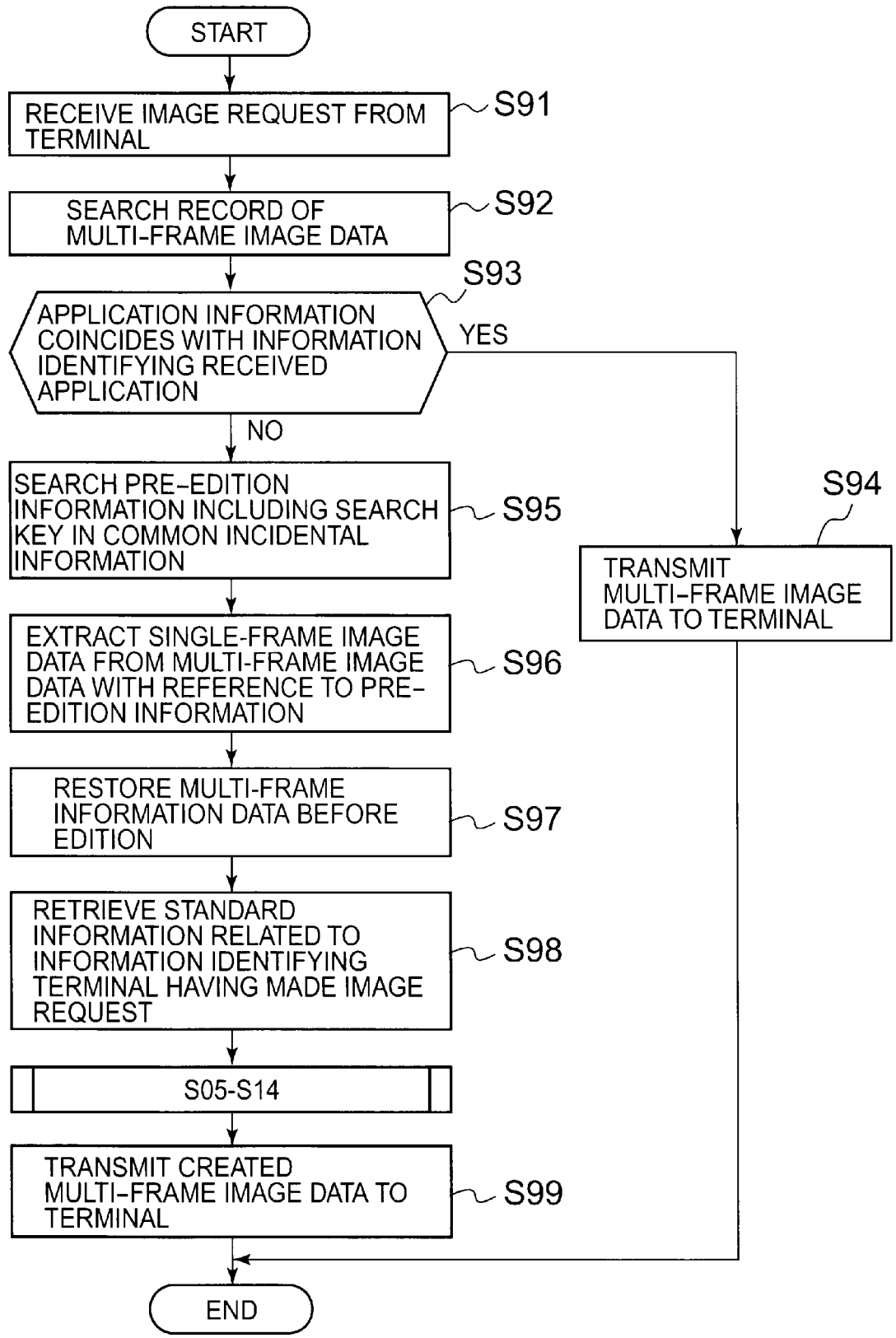
FIG. 21 is a flow chart showing operations of restoring and reediting multi-frame image data.

FIG. 21 is a flow chart showing the operation of restoring and reediting multi-frame image data. To the standard information table, information identifying a terminal (not illustrated) is linked. First, when receiving an image request from a terminal in step S91, the database management system searches a record of multi-frame image data in step S92. In step S93, the database management system checks whether application information included in the record coincides with information identifying the application received from the terminal having made the image request. In a case where the application information coincides (S93, Yes), the multi-frame image data is transmitted to the terminal in step S94.

On the other hand, in a case where there is no coincident record (S93, No), the generator 130, in step S95, searches pre-edition information including patient information or the like that is the search key transmitted by the terminal in the common incidental information.

When the pre-edition information is found, the generator 130, in step S96, refers to each of incidental information stored in the frame information region of the pre-edition information, and extracts single-frame image data corresponding to the incidental information from multi-frame image data stored in the database 150. After extracting the single-frame image data, the generator 130 combines the extracted single-frame image data with the pre-edition information to restore the multi-frame image data before edition in step S97. After restoring the multi-frame image data, the generator 130 retrieves standard information linked to the information identifying the terminal having made the image request in step S98, and executes the process from step S05 to step S14 on the standard information, thereby generating multi-frame image data in which image data necessary for the terminal having made the image request are compiled. The transmitter 160 transmits the generated multi-frame image to the terminal in step S99. In a case where the multi-frame image of the edition source received from the image diagnosis apparatus 1 has not been deleted, it is not necessary to restore, and it is enough to edit the multi-frame image.

The image archive apparatus 100 of each of the embodiments described above may be configured to, not only when receiving data but also regularly, execute the editing process on archived multi-frame image data or single-frame image data. The generator 130 stores preset time information and, when time measured by a clock IC or the like reaches the time information, retrieves the multi-frame image data or single-frame image data within the database 150 to execute the editing process. Further, it is also possible to configure to execute the editing process during idle time in processing by the image archive apparatus 100, that is, when the load is light. At this moment, if the priority information, the terminal information, or the standard information has been changed, the multi-frame image data or single-frame image data within the database 150 is reedited into a single unit of multi-frame image data according to the change, thus enabling speedy adaptation to changes in the network environment while continuously taking advantage of the convenience of multi-frame image data.

What is claimed is:

1. An image archive apparatus, comprising:
   a receiver configured to receive image data including incidental information;
   a storage configured to store a condition regarding a characteristic of a group of plural frames of images for generating multi-frame image data including plural frames of images in one file from the image data;
   a determining unit configured to compare the condition with the incidental information included in the image data received by the receiver to determine whether the condition complies with the incidental information;
   a generator configured to generate the multi-frame image data in which image data that complies with the condition are compiled; and
   an archive configured to archive the multi-frame image data generated by the generator;
   wherein:
   the storage stores plural types of conditions; and
   the generator stores a priority condition and generates multi-frame image data based on the condition satisfying the priority condition,
   wherein:
   the storage correlates and stores plural types of conditions and information on a number of terminals for displaying the multi-frame image data;
   the priority condition is a condition regarding the number of the terminals; and
   the generator generates multi-frame image data based on the condition related to the information on the number of the terminals satisfying the priority condition.

2. The image archive apparatus according to claim 1, wherein:
   the generator is configured not to include image data that does not satisfy the characteristic represented by the condition into the multi-frame image data generated thereby.

3. The image archive apparatus according to claim 1, wherein:
   the condition represents a characteristic of a group of image data processed by an application software functioning on a terminal, the terminal for displaying the multi-frame image data.

4. An image archive apparatus, comprising:
   a receiver configured to receive image data including incidental information;
   a storage configured to store a condition regarding a characteristic of a group of plural frames of images for generating multi-frame image data including plural frames of images in one file from the image data;
   a determining unit configured to compare the condition with the incidental information included in the image data received by the receiver to determine whether the condition complies with the incidental information;
   a generator configured to generate the multi-frame image data in which image data that complies with the condition are compiled; and
   an archive configured to archive the multi-frame image data generated by the generator;
   wherein:
   the storage stores plural types of conditions; and
   the generator stores a priority condition and generates multi-frame image data based on the condition satisfying the priority condition,
   wherein:
   the storage correlates and stores plural types of conditions and information on a type of the image archive apparatus;
   the priority condition is information indicating the type of the image archive apparatus; and
   based on the condition related to the information indicating the type of the image archive apparatus having imaged the received multi-frame image data, the generator generates multi-frame image data.

5. An image archive apparatus, comprising:
   a receiver configured to receive image data including incidental information;
   a storage configured to store a condition regarding a characteristic of a group of plural frames of images for generating multi-frame image data including plural frames of images in one file from the image data;
   a determining unit configured to compare the condition with the incidental information included in the image data received by the receiver to determine whether the condition complies with the incidental information;
   a generator configured to generate the multi-frame image data in which image data that complies with the condition are compiled; and
   an archive configured to archive the multi-frame image data generated by the generator;
   wherein:
   the storage stores plural types of conditions; and
   the generator stores a priority condition and generates multi-frame image data based on the condition satisfying the priority condition,
   wherein:
   the storage correlates and stores plural types of conditions and information indicating a frequency of image requests;
   the priority condition is information indicating a specified frequency; and
   based on the condition related to the information indicating the frequency of image requests satisfying the specified frequency, the generator generates multi-frame image data.

* * * * *